United States Patent
Gilman et al.

(10) Patent No.: US 6,269,699 B1
(45) Date of Patent: Aug. 7, 2001

(54) DETERMINATION OF ACTUAL DEFECT SIZE IN CATHODE SPUTTER TARGETS SUBJECTED TO ULTRASONIC INSPECTION

(75) Inventors: Paul S. Gilman, Suffern, NY (US); Alfred Snowman, Englewood, NJ (US); Andre Desert, Spring Valley, NY (US)

(73) Assignee: Praxair S. T. Technology, Inc., North Haven, CT (US)

( * ) Notice: Subject to any disclaimer, the term of this patent is extended or adjusted under 35 U.S.C. 154(b) by 0 days.

(21) Appl. No.: 09/431,745

(22) Filed: Nov. 1, 1999

(51) Int. Cl.[7] .................................................. G01N 29/10
(52) U.S. Cl. ........................... 73/601; 73/1.82; 73/602; 73/866
(58) Field of Search ............................ 73/602, 1.82, 597, 73/598, 599, 600, 601, 620, 627, 866

(56) References Cited

U.S. PATENT DOCUMENTS

| | | | | |
|---|---|---|---|---|
| 3,677,073 | * | 7/1972 | Morgan | 73/620 |
| 4,011,748 | * | 3/1977 | Bond et al. | 73/601 |
| 4,611,493 | * | 9/1986 | Muth | 73/601 |
| 4,614,410 | * | 9/1986 | Ikenaga et al. | 73/601 |
| 5,319,977 | * | 6/1994 | Quate et al. | 73/620 |
| 5,406,850 | * | 4/1995 | Bouchard et al. | 73/620 |
| 5,887,481 | | 3/1999 | Leroy et al. | 73/866 |
| 5,955,673 | * | 9/1999 | Leroy et al. | 73/602 |

* cited by examiner

Primary Examiner—Daniel S. Larkin
Assistant Examiner—Rose M. Miller
(74) Attorney, Agent, or Firm—Blake T. Biederman

(57) ABSTRACT

A method for determining actual size of internal target defects by ultrasonic inspection is provided in which the amplitude of signals generated by ultrasonic inspection are compared to metallurgical size measurements obtained through the use of optical microscopes or scanning electron microscopes or scanning election microscopes. From this comparison, a correlation factor may be obtained to determine the accuracy of the ultrasonic measurements. For a particular sputter target material, defect sizes obtained by ultrasonic inspection may then be multiplied by the correlation factor to determine the actual defect size for that defect. The use of actual defect sizes to determine defect sizes from ultrasonic inspection provides a more accurate determination of defect sizes than prior methods and provides a reliable means for accepting or rejecting targets for critical circuit manufacturing operations.

19 Claims, No Drawings

DETERMINATION OF ACTUAL DEFECT SIZE IN CATHODE SPUTTER TARGETS SUBJECTED TO ULTRASONIC INSPECTION

FIELD OF THE INVENTION

This invention relates to a method for nondestructive testing of sputter targets for internal defects, more specifically a method for determining actual inclusion size of defects measured by ultrasonic testing.

BACKGROUND OF THE INVENTION

Cathodic sputtering is a deposition process involving ion bombardment of a target composed of a material to be deposited onto a substrate. The target forms part of a cathode assembly in an evacuated chamber containing an inert gas, such as argon. An electric field supplied between the cathode assembly and an anode in the chamber, and the gas is ionized by collision with electrons ejected from the surface of the cathode, forming a plasma between the target surface and the substrate. The positive gas ions are attracted to the cathode surface, and particles of material dislodged when the ions strike the target then traverse the enclosure and deposit as a thin film onto a substrate or substrates positioned on a support maintained at or near anode potential.

This deposition technique has been applied extensively in electronics for the coating of semiconductor silicon wafers with aluminum or an aluminum alloy in the manufacture of integrated circuits. The manufacture of integrated circuits with a high level of integration, for example, DRAM memories with a capacity greater than 4 MB, requires the deposition of metallic interconnection layers of small thickness (approximately 1 $\mu$m), which are then etched to form extremely fine lines (less than 0.5 $\mu$m in width) allowing individual access to each memory position. Under these conditions, any defect in the metallization layer, whose size is close to the width of an interconnection line, can lead to a material defect during the etching operation of the integrated circuit, and lead to the rejection of the integrated circuit.

In the case of current and future generations of ultra-large-scale integrated circuits, for example, the DRAM memories of 16 MB or more, the fineness of etching has been considerably stressed, and the width of the line has been brought to a few tenths of a micron, on the order of 0.2–0.5 $\mu$m. Defects, such as inclusions, from the target deposited on the semiconductor substrate during cathodic sputtering have become a major cause for rejection of integrated circuits, and each year these defects cost the worldwide electronics industry considerable sums of money.

To reduce the number of thin film coated substrates rejected because of etching defects due to inclusions or other defects in the sputter target, aluminum and aluminum alloy cathode sputter targets are inspected nondestructively for such internal defects. Ultrasonic test methods are typically used for this inspection in which the target is immersed in a liquid and the material is scanned for defects. Typically, the defect size is determined by comparing the amplitude of the signal generated with the signal from an artificial defect of known size machined into a reference target blank. As described in U.S. Pat. No. 5,887,481, an ultrasound sensor or probe is calibrated with respect to artificial defects consisting of flat-bottomed holes having a diameter of 0.1 mm machined into a target composed of an identical alloy with metallurgical characteristics similar to those of the product to be tested. The targets to be tested are then immersed in liquid and the amplitude of the ultrasound echo obtained is compared with the amplitude of the artificial defect to determine the relative size of the defects. Also, the number of echoes exceeding the amplitude corresponding to the artificial defect of 0.1 mm may be counted. By this method, targets having too many defects per unit volume or having defects of large size can be thrown out to prevent the use of such targets which can have a negative effect on sputtered film quality.

A disadvantage of this method is that the maximum allowable defect size in sputter targets that must meet current line width sizes is approximately a factor of 10 smaller than the smallest artificial defect sizes that can feasibly be machined into the reference target blanks. Thus, there is likely to be a great disparity between the size of the actual defects and the size of the artificial defect to which it is being compared.

There is thus a need to develop a method for determining actual defect sizes in cathode sputtering targets subjected to ultrasonic inspection that is accurate and relatively easy to carry out.

SUMMARY OF THE INVENTION

The present invention provides a method for non-destructively testing sputter targets by ultrasonic inspection to determine the actual size of defects within the target material. To this end, and in accordance with the principles of the present invention, ultrasonic signals generated from actual defects of unknown size are compared with metallurgical size measurements of the same actual defects. For the metallurgical size measurement, an actual defect may be measured by grinding and polishing away the surface of the target metal until the defect is exposed and using a scanning electron microscope, optical microscope or other optical measuring device to determine the size. From the comparison of the ultrasonic measurement and metallurgical measurement, a correlation factor may be obtained for a particular sputter target material that when multiplied by ultrasonic signals generated from any sputter target of that material will provide accurate, reliable estimates of actual defect sizes. When the number of internal defects having a large actual size exceed a maximum acceptable number, the sputter target may be discarded to avoid etching defects in thin film coated substrates.

These and other objects and advantages of the present invention shall become more apparent from the accompanying detailed description.

DETAILED DESCRIPTION

A sputter target is immersed in a liquid and scanned for internal defects using ultrasonic scanning equipment. The sputter target is typically mounted on a fixture, which is lowered into the liquid. The ultrasonic inspection is conducted at a frequency of about 5–50 MHz, and advantageously between 15–25 MHz, with the ultrasonic beam focused to scan across the thickness of the target. Defects within the material, such as inclusions, generate signals, or waves, and this information is fed to a computer, which plots the data. The amplitudes of the ultrasonic waves are measured and then recorded.

This same target is then subjected to metallurgical testing by mounting sections of the target, such as in a plastic mold, and grinding and polishing away the target metal surface in small layers until one or more of the defects are exposed. This may be accomplished with conventional grinding and polishing wheels that use progressively finer abrasive papers. If desired, conventional chemical etching may also be performed to further achieve exposure of the inclusions. The size of the defects are measured with the aid of a measuring device measuring device, such as a scanning electron microscope (SEM) or microscope, and preferably with the aid of an SEM at a magnification of about 1000× –2000×, which is capable of accurately determining extremely small defect sizes. Once the metallurgical size measurement is obtained, it is compared to the amplitude of the signal generated from the ultrasonic inspection. A correlation factor may then be determined that when multiplied by the ultrasonic measurement provides the actual size of the defect as measured by the metallurgical testing method. Once the correlation factor has been determined for a particular sputter target material, other sputter targets of that same material may be subjected to ultrasonic inspection, and the amplitudes of the signals generated thereby may then be multiplied by the correlation factor to determine actual defect sizes. Thus, once a correlation factor has been determined, metallurgical testing need not be performed again to accurately determine the size of the defects within the sputter target material.

By way of example, an Al/0.5%Cu sputter target was examined for inclusions and other defects using ultrasonic transmission at a frequency in the range of about 15–25 MHz. Four defects were selected and the amplitudes of the signals generated showed an average defect size of 250 $\mu$m. This sputter target blank was then cut up and samples were taken from the areas showing the defects. These samples were first mounted, ground and polished and then examined microscopically with an SEM/EDAX (electron discharge analyzer) at a magnification of 1000×–2000× by which a number of defects were located. Micrographic pictures were taken and the defects measured thereby had an average size of 25 $\mu$m. From this data, the correlation factor was determined to be 0.1. Thus, for Al/0.5%Cu sputter target materials, the amplitudes of signals generated from ultrasonic inspection may be multiplied by the correlation factor of 0.1 to determine the actual defect size for each defect detected.

The method of the present invention permits a more accurate and representative determination of defect size for sputter targets submitted for ultrasonic inspection than prior methods. Because this method uses actual defects rather than artificial machined defects, it avoids the disadvantages of the prior art method associated with the artificial defects and provides a better means of accepting or rejecting targets for critical circuit manufacturing operations, thus limiting the possibility of shipping defective sputter targets to customers. Furthermore, the method of the present invention reduces the time and cost required for defect evaluation, as each defect detected need not be compared to a reference target defect to determine its size.

It is to be understood that the correlation factor will differ from metal to metal and alloy to alloy, and thus, the initial correlation test should be run for a particular type of sputter target material to determine the corresponding correlation factor for that particular material. For aluminum and aluminum alloys with low alloy content, the correlation factor has been determined to be about 0.1. Once the correlation factor is determined, the correlation test need not be run again for that particular material. The principles of the present invention apply to any type of metal or alloy used for the manufacture of sputter targets.

Once the actual defect sizes are determined for internal defects detected within a sputter target material, a decision may be made to accept or reject the target. Typically, sputter targets are discarded when the number of internal defects having an actual size greater than a predetermined maximum size exceeds a maximum acceptable amount. In one embodiment of the present invention, at current line widths of 0.2–0.5 $\mu$m, the predetermined maximum defect size is about 50 $\mu$m, and the number of internal defects having an actual size greater than that predetermined size should not exceed the maximum acceptable amount of 25 on a 12 inch diameter target.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A method for non-destructively determining the actual size of target defects submitted for ultrasonic inspection, comprising the steps of:

obtaining an ultrasonic measurement of the size of an actual internal defect having an unknown size in a sputter target material by scanning the material and recording an amplitude of a signal generated;

obtaining a metallurgical measurement of the size of the internal defect by exposing the internal defect and measuring the actual size thereof with the use of a measuring device; and correlating the ultrasonic measurement with the metallurgical measurement to obtain a correlation factor for the sputter target material that when multiplied by a future ultrasonic measurement of an internal defect will provide the actual size for that defect.

2. The method of claim 1, wherein the sputter target material is aluminum or an aluminum alloy.

3. The method of claim 1, wherein the ultrasonic measurement is obtained by scanning the material at a frequency of 5–50 MHz.

4. The method of claim 1, wherein the ultrasonic measurement is obtained by scanning the material at a frequency of 15–25 MHz.

5. The method of claim 1, wherein the metallurgical measurement is obtained by grinding and polishing away one or more surface layers of the sputter target material until the internal defect is exposed.

6. The method of claim 1, wherein the metallurgical measurement is obtained by exposing the defect and measuring the actual size with the use of a scanning electron microscope.

7. The method of claim 1, wherein the metallurgical measurement is obtained by exposing the defect and measuring the actual size with the use of an optical microscope.

8. A method for eliminating defective targets having an unacceptable amount of internal defects larger than a predetermined size, comprising the steps of:

obtaining an ultrasonic measurement of the size of an actual internal defect having an unknown size in a sputter target material by scanning the material and recording an amplitude of a signal generated;

obtaining a metallurgical measurement of the size of the internal defect by exposing the internal defect and measuring the actual size thereof with the use of an optical measuring device;

correlating the ultrasonic measurement with the metallurgical measurement to obtain a correlation factor for the sputter target material that when multiplied by a future ultrasonic measurement of an internal defect will provide the actual size for that defect;

obtaining an ultrasonic measurement for each of one or more internal defects having an unknown size within a sputter target comprised of the sputter target material;

multiplying the ultrasonic measurement for each internal defect by the correlation factor to determine the actual size of each internal defect; and accepting a sputter target in which the number of the internal defects having an actual size greater than the predetermined size is less than a maximum acceptable amount.

9. The method of claim 8, wherein the sputter target material is aluminum or an aluminum alloy.

10. The method of claim 8, wherein the ultrasonic measurement is obtained by scanning the material at a frequency of 5–50 MHz.

11. The method of claim 8, wherein the ultrasonic measurement is obtained by scanning the material at a frequency of 15–25 MHz.

12. The method of claim 8, wherein the metallurgical measurement is obtained by grinding and polishing away one or more surface layers of the sputter target material until the internal defect is exposed.

13. The method of claim 8, wherein the metallurgical measurement is obtained by exposing the defect and measuring the actual size with the use of a scanning electron microscope.

14. The method of claim 8, wherein the metallurgical measurement is obtained by exposing the defect and measuring the actual size with the use of an optical microscope.

15. The method of claim 8, wherein the predetermined size is less than about 50 $\mu$m.

16. The method of claim 8, wherein an unacceptable amount is greater than about 25.

17. A method for eliminating defective aluminum targets having an unacceptable amount of internal defects larger than a predetermined size, comprising the steps of:

obtaining an ultrasonic measurement for each of one or more internal defects having an unknown size within a sputter target comprised of aluminum or an aluminum alloy;

multiplying the ultrasonic measurement for each internal defect by a correlation factor of about 0.1 to determine the actual size of each internal defect; and accepting a sputter target in which the number of the internal defects having an actual size greater than the predetermined size is less than a maximum acceptable amount.

18. The method of claim 17, wherein the predetermined size is less than about 50 $\mu$m.

19. The method of claim 17, wherein an unacceptable amount is greater than about 25.

\* \* \* \* \*